United States Patent [19]

Endo et al.

[11] 4,368,314
[45] Jan. 11, 1983

[54] CURABLE COMPOSITION COMPRISING SPIRO-ORTHOESTER COMPOUND

[75] Inventors: Takeshi Endo, Yokohama; Kiyokazu Mizutani, Inasawa; Takahisa Ogasawara, Tokai, all of Japan

[73] Assignee: Toagoesi Chemical Industry Co., Ltd., Tokyo, Japan

[21] Appl. No.: 295,739

[22] Filed: Aug. 24, 1981

[30] Foreign Application Priority Data

Aug. 29, 1980 [JP] Japan .................. 55-118283
Oct. 13, 1980 [JP] Japan .................. 55-142042

[51] Int. Cl.³ .................. C08G 59/26; C08G 63/42
[52] U.S. Cl. .................. 528/89; 528/88; 528/90; 528/91; 528/92; 528/93; 528/94; 528/96; 528/100; 528/104; 528/110; 528/112; 528/179; 528/180; 528/354; 528/359; 528/361; 528/365; 528/366; 525/504; 525/506; 525/507
[58] Field of Search .................. 528/88, 89, 90, 91, 528/92, 93, 94, 96, 100, 104, 110, 112, 179, 180, 354, 359, 361, 365, 366; 525/507, 504, 506

[56] References Cited

U.S. PATENT DOCUMENTS

| | | | |
|---|---|---|---|
| 3,381,053 | 4/1968 | Vogt et al. .................. | 528/96 |
| 3,388,098 | 6/1968 | Harding .................. | 528/96 |
| 3,401,147 | 9/1968 | Smith et al. .................. | 528/96 |
| 3,539,591 | 11/1970 | Batzer et al. .................. | 528/365 X |
| 3,884,944 | 5/1975 | Renner et al. .................. | 528/365 X |

*Primary Examiner*—Earl A. Nielsen
*Attorney, Agent, or Firm*—Cooper, Dunham, Clark, Griffin & Moran

[57] ABSTRACT

A curable composition comprising:
(A) at least one spiro-orthoester compound having at least one spiro-orthoester group represented by the formula: [I]

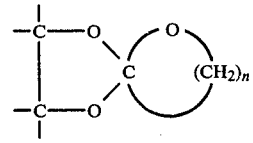

wherein n is an integer of 3–5,
(B) at least one curing agent selected from the group consisting of organic polybasic acids and their anhydrides,
(C) optionally, an epoxy compound having at least one epoxy group, and
(D) optionally a cationic polymerization catalyst when the composition comprises ingredient (C).

Said composition is small in shrinkage on curing, and provides a cured product of high dimensional accuracy when used as a molding material.

29 Claims, No Drawings

CURABLE COMPOSITION COMPRISING SPIRO-ORTHOESTER COMPOUND

This invention relates to a curable composition comprising a spiro-orthoester compound having at least one spiro-orthoester group (said compound is, hereinafter, referred to simply as "spiro-orthoester"). More particularly, this invention relates to a curable composition comprising a spiro-orthoester, an organic polybasic acid curing agent, and optionally an epoxy compound, and further optionally a cationic polymerization catalyst when the composition comprises said epoxy compound.

It is well known that thermosetting resins generally shrinks considerably in volume when cured. For example, an epoxy resin shows a volume shrinkage of about 3–6% on curing, though it belongs to a class giving the smallest shrinkage among many resins.

If the volume shrinkage on curing is great, such problems arise that dimensional accuracy is unsatisfactory when the resin is used as a molding material, that an embedded material undergoes a strain due to shrinkage and the adhesion to a mold drops or a gap is formed between the resin and a mold when the resin is used as a casting material, and so on. Further, various problems can arise in connection with such a use that the adhesion to a substrate drops and a warpage appears due to the internal strain when the resin is used as a coating material and that a drop in adhesion, a warpage, a deformation, etc. take place due to the internal strain when the resin is used as an adhesive.

For these reasons, it is intensely desired to develop a curable composition quite small in volume shrinkage on curing.

Spiro-orthoesters per se are mentioned in W. J. Bailey, Journal of Macromolecular Science, Chemistry, A9(5), 849–865 (1975) and some other papers. However, the preset inventors have conducted various studies on the chemical characteristics of spiro-orthoesters to discover that said compounds undergo not only a cationic polymerization in the presence of a cationic polymerization catalyst but also a ring-opening polymerization in the presence of an organic acid curing agent and, in addition, they give a very small volume shrinkage on curing.

It is an object of this invention to provide a curable composition which is quite small in volume shrinkage on curing and is suitable for use as a molding material, a casting material, an adhesive or the like.

Other objects and advantages of this invention will become apparent from the following description.

According to this invention, there is provided a curable composition comprising:

(A) at least one spiro-orthoester compound having at least one spiro-orthoester group represented by the formula [I]:

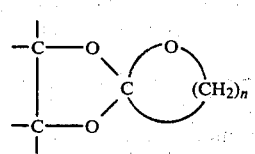

[I]

wherein n is an integer of 3–5, (B) at least one curing agent selected from the group consisting of organic polybasic acids and their anhydrides, (C) optionally, an epoxy compound having at least one epoxy group, and (D) optionally a cationic polymerization catalyst when the composition comprises ingredient (C).

The spiro-orthoesters can be produced, for example, by the reaction of an epoxy compound and a lactone. The process for producing them is as follows: A lactone such as γ-butyrolactone, δ-valerolactone or ε-caprolactone and a catalyst such as $BF_3OEt_2$ are dissolved in an appropriate solvent such as carbon tetrachloride, methylene chloride or the like, and a solution of an epoxy compound in an appropriate solvent is dropped thereinto to react them while controlling the reaction temperature. In this case, the reaction temperature is generally in the range of 0°–30° C. and the lactone and the epoxy compound are usually used in a proportion of 1 equivalent or more of the lactone per equivalent of the epoxy group, though the above proportion is not critical. If desired, however, the lactone may be employed in a proportion smaller than 1 equivalent per equivalent of the epoxy group.

The isolation of spiro-orthoester from the reaction mixture is effected either by directly removing the solvent or by washing the mixture with an alkali to remove the lactone and then removing the solvent. If necessary, there may also be effected thereafter distillation under reduced pressure or purification with a solvent such as recrystallization.

The spiro-orthoester used in this invention may contain free epoxy group which is the unreacted epoxy group of the starting epoxy compound. Preferably, the amount of said free epoxy group is not more than 20 mole percent based on the epoxy group in the starting epoxy compound.

The process for producing the spiro-orthoester can generally be illustrated as follows:

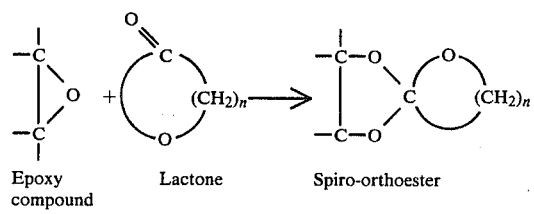

Epoxy compound  Lactone  Spiro-orthoester

As an example of the reaction, there is a reaction between phenyl glycidyl ether and γ-butyrolactone, which can be illustrated as follows:

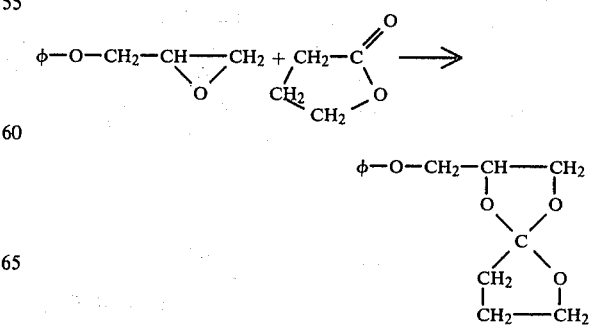

wherein φ represents a phenyl group. Another example of the reaction is a reaction between an alicyclic epoxy compound and ε-caprolactone, which can be illustrated as follows wherein Chissonox 221 (a trade name of Chisso Co., Ltd. for 3′, 4′-epoxycyclohexylmethyl-3,4-epoxycyclohexylcarboxylate) is used as the alicyclic epoxy compound:

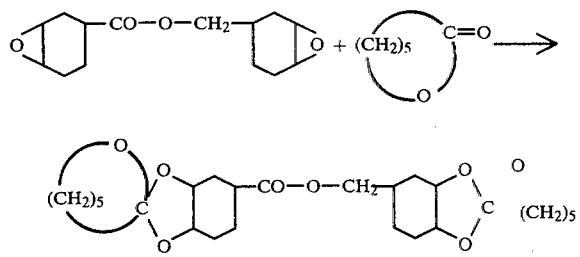

Further, derivatives of the spiro-orthoesters produced from epoxy compounds and lactones can also be used in this invention. As an example of said derivatives, there may be mentioned a methylene-containing spiro-orthoester produced by the dehydrochlorination of chloromethyl spiro-orthoester, which can be represented by the formula:

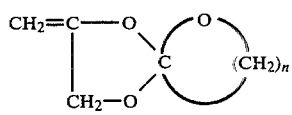

wherein n is an integer of 3–5.

The above-mentioned compound can be produced, for example, be dehydrochlorination of 2-chlomethyl-1,4,6-trioxaspiro[4,6]undecane. This reaction can be illustrated as follows:

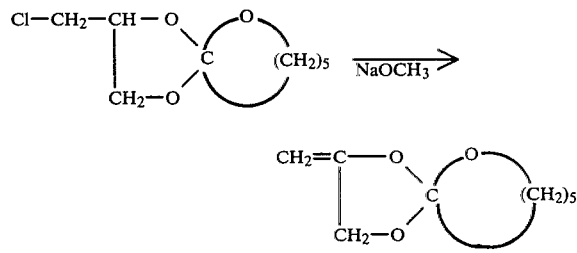

Further, the spiro-orthoester used in this invention also includes the spiro-orthoesters having spiro-orthoester group introduced into the molecule by the de-sodium halide reaction. An example thereof is the de-sodium bromide reaction between the sodium salt of phenol and 2-bromomethyl-1,4,6-trioxaspiro[4,4]nonane, which can be illustrated as follows:

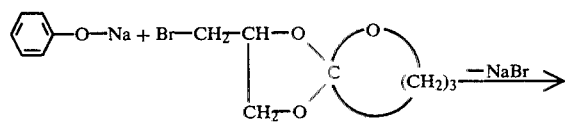

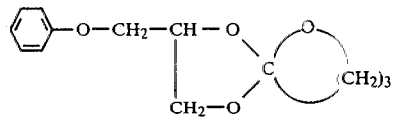

Though the cationic polymerization of a spiro-orthoester is described in the above-mentioned literature reference and the like, the fact that spiro-orthoesters can undergo a ring-opening polymerization by the action of an organic acid curing agent alone or in combination with an epoxy compound has not been known, and the present inventors are the first to discover this fact.

The preferable spiro-orthoesters used in this invention are compounds represented by the following formula [II] which have at least one spiro-orthoester group in the molecule:

$$Y\text{-}(A)_m \qquad [II]$$

wherein m is an integer of at least 1, and A represents

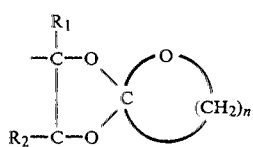

or

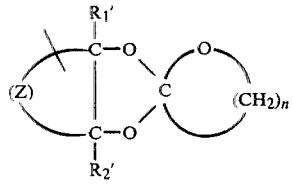

wherein (Z) represents a substituted or unsubstituted cycloalkylene group, n represents an integer of 3–5, Y represents the residue given by depriving an epoxy compound of the epoxy group (including depriving an alicyclic epoxy compound of the endo-epoxy group); and $R_1$, $R_2$, $R_3$, $R_1'$ and $R_2'$ independently represent hydrogen atoms, alkyl groups, haloalkyl groups or alkenyl groups, and Y and $R_1$, when taken together, may form a methylene group.

The spiro-orthoester used in the composition of this invention includes the following compounds:

1,4,6-trioxaspiro[4,4]nonane, 2-methyl-1,4,6-trioxaspiro[4,4]nonane, 2-chloromethyl-1,4,6-trioxaspiro[4,4]nonane, 2-phenoxymethyl-1,4,6-trioxaspiro-[4,4]nonane, 1,4,6-trioxaspiro[4,5]decane, 2-chloromethyl-1,4,6-trioxaspiro[4,6]undecane, 2,3-dimethyl-1,4,6-trioxaspiro[4,6]undecane, 2-methylene-1,4,6-trioxaspiro[4,4]nonane, 2-methylene-1,4,6-trioxaspiro[4,6]undecane, 2-phenyl-1,4,6-trioxaspiro[4,6]undecane and the like;

Spiro-orthoesters produced by the reaction of a lactone and an epoxy resin having, on the average, at least one glycidyl or β-methylglycidyl ether group (glycidyl or β-methylglycidyl is hereinafter referred to collectively as "(β-methyl)-glycidyl") in the molecule obtained by reacting epichlorohydrin or β-methylepichlorohydrin (hereinafter, both are collectively referred to as "(β-methyl)-epichlorohydrin") with 2,2-bis(4'-hydroxyphenyl)propane (usually called Bisphenol A); halogenated Bisphenol A; bis(4-hydroxyphenyl)methane (usually called Bisphenol F); resorcinol or tetrahydroxyphenylmethane; a novolac type polyfunctional phenol obtained by the condensation of phenol or cresol and formaldehyde; a phenolic compound such as phenol, cresol, t-butylphenol or the like; or an alcohol compound such as butyl alcohol, allyl alcohol, ethylene glycol, polyethylene glycol, 2,2-bis(4'-hydroxycyclohexyl)propane, glycerin, 1,1,1-trimethylolpropane or the like;

spiro-orthoesters produced by the reaction of a lactone and an epoxy resin having, on the average, at least one (β-methyl)-glycidyl ester group in the molecule obtained by reacting (β-methyl)-epichlorohydrin with a compound having a carboxylic acid group such as benzenemonocarboxylic acid, adipic acid, adipic acid, phthalic acid, hexahydrophthalic acid, tetrahydrophthalic acid, or the like;

spiro-orthoesters produced from a lactone and an alicyclic epoxy resin having, on the average, at least one endo-epoxy group in the molecule such as Chissonox 201, 221, 289, 206, 207 and 1222 [trade names of Chisso. Co., Ltd. for 3',4'-epoxy-6'-methylcyclohexyl methyl-3,4-epoxy-6-methylcyclohexylcarboxylate, 3',4'-epoxycyclohexylmethyl-3,4-epoxycyclohexylcarboxylate, bis(6-methyl-3,4-epoxycyclohexylmethyl) adipate, 1-epoxyethyl-3,4-epoxycyclohexane(vinylcyclohexane dioxide, (dicyclopentadiene dioxide and

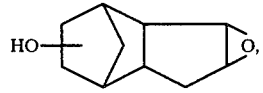

respectively] or Araldite CY-175, CY-178 and CY-179 [trade names of Ciba Products Co., Ltd. for

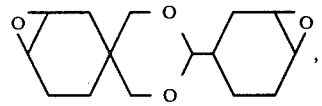

bis(6-methyl-3,4-epoxycyclohexylmethyl)adipate and 3',4'-epoxycyclohexylmethyl-3,4-epoxycyclohexylcarboxylate, respectively] and Araldite CY-176 (a trade name of Ciba Products Co., Ltd.), or the like;

spiro-orthoesters produced from a lactone and an epoxidized olefin, epoxydized polybutadiene, epoxydized vegetable oil; a nitrogen-containing epoxy compound such as an aniline modified epoxy compound; or a nitrogen-containing heterocyclic epoxy compound obtained from an isocyanuric acid derivative, a hydantoin derivative, an imidazoline derivative or the like; and mixtures of the above-mentioned spiro-orthoesters.

In the composition of this invention, the spiro-orthoester may, if desired, be used in combination with an epoxy compound. As said epoxy compound, there may be used epoxy compounds having one or more epoxy groups in the molecule, such as (β-methyl)-glycidyl ethers, or poly[(β-methyl)-glycidyl] ethers obtained by reacting (β-methyl)-epichlorohydrin with 2,2-bis(4'-hydroxyphenyl)propane, halogenated Bisphenol A, bis(4-hydroxyphenyl)methane, resorcinoal or tetrahydroxyphenylmethane; or with a novolac type polyfunctional phenol obtained by the condensation of phenol or cresol and formaldehyde; or with a phenolic compound such as phenol, cresol, t-butylphenol or the like. Further, (β-methyl)-glycidyl ethers and poly[(β-methyl)-glycidyl] ethers obtained by reacting (β-methyl)-epichlorohydrin with an alcohol such as butyl alcohol, allyl alcohol, ethylene glycol, polyethylene glycol, 2,2-bis(4'-hydroxycyclohexyl)propane, glycerin, 1,1,1-trimethylolpropane or the like may also be used. In addition to the above, (β-methyl)-glycidyl esters and poly[(β-methyl)-glycidyl] esters obtained by reacting (β-methyl)-epichlorohydrin with a compound having a carboxyl group such as benzenemonocarboxylic acid, adipic acid, sebacic acid, phthalic acid, hexahydrophthalic acid, tetrahydrophthalic acid or the like may also be used. Further, there may also be used an epoxidized olefin, epoxidized polybutadiene, an epoxidized vegetable oil, an epoxidized cyclopentadiene compound, a nitrogen-containing epoxy compound such as aniline-modified epoxy compound; a nitrogen-containing heterocyclic epoxy compound obtained from an isocyanuric acid derivative, a hydantoin derivative or an imidazoline derivative; a styrene oxide obtained from a monounsaturated compound; and an endo-epoxy type compound synthesized by the oxidation of an intramolecular double bond such as Chissonox 201, 221, 289, 206, 207, or 1222 and Araldite CY-175, CY-176, CY-178 or CY-179 or the like. In the composition of this invention, one or more epoxy compounds as mentioned above may be used as the ingredient (C).

In the composition of this invention, the epoxy compound is used in a proportion of not more than 90% by weight based on the weight of spiro-orthoester. If the proportion of the epoxy compound is larger than 90% by weight, shrinkage on curing and adhesion unsatisfactory. Further, taking the glass transition temperature and heat resistance of cured product into consideration, the amount of epoxy compound used is preferably 5% by weight or more and more preferably in the range of 70–10% by weight.

The organic polybasic acids and their anhydrides which are used as the curing agent in the composition of this invention cover all the substances conventionally used as curing agents for epoxy compounds, and include succinic acid, methylsuccinic acid, dodecenylsuccinic acid, dichlorosuccinic acid, azelaic acid, sebacic acid, itaconic acid, maleic acid, citraconic acid, phthalic acid, tetrahydrophthalic acid, methyltetrahydrophthalic acid, hexahydrophthalic acid, methylhexahydrophthalic acid, endomethylenetetrahydrophthalic acid, methylendomethylenetetrahydrophthalic acid, tricarballylic acid, trimellitic acid, pyromellitic acid, cyclopentane-1,2,3,4-tetracarboxylic acid, benzophenone-3,3',4,4'-tetracarboxylic acid, and their anhydrides. Further, there may also be used mixtures of two or more of them; their mixtures with monobasic acid anhydrides, and derivatives of the above-mentioned polybasic acids or their anhydrides, which derivatives have a carboxylic acid structure or an acid anhydride structure at the molecular terminal or on the side chain such as maleic anhydride-linoleic acid adduct, and the like.

The proportion of the curing agent contained in the composition of this invention may be varied depending on the chemical properties of the curing agent as well as on the properties required for the curable composition and cured product. For example, when a polycarboxylic acid or its acid anhydride is used as the curing agent, said carboxylic acid or carboxylic acid anhydride is usually used in an amount of about 0.1–1.5 equivalents, preferably about 0.2–1.3 equivalents, and more preferably about 0.3–1.2 equivalents per equivalent of the total sum of the equivalent of spiro-orthoester group and the equivalent of epoxy group.

If necessary, an appropriate curing accelerator may be used for the sake of further shortening the curing time. As appropriate curing accelerators, there may be menioned tertiary amines, quaternary ammonium salts, imidazole compounds, pyridine, dicyandiamide, chelate compounds, metallocenes and the like.

The amount of the curing accelerator is usually 0.2–3 parts by weight per 100 parts by weight of the total sum of spiro-orthoester, epoxy compound and curing agent. Though the curing temperature is not critical, the curing is usually carried out at a temperature ranging from room temperature to 200° C.

When an epoxy compound is used in the composition of this invention, a part or the whole of the organic acid curing agent may be replaced by a cationic polymerization catalyst. As said cationic polymerization catalyst, there may be used aromatic diazonium salts such as $\phi-N^+\equiv N.PF_6^-$, $\phi-N^+\equiv N.BF_4^-$ and the like; aromatic halonium salts such as $\phi-I^+-\phi.BF_4^-$ and the like; aromatic onium salts of the elements of Group Va of the Periodic Table such as

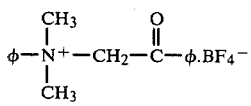

and the like; aromatic onium salts of the elements of Group VIa of the Periodic Table such as

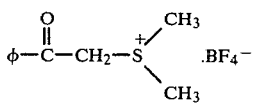

and the like; dicarbonyl chelates of the elements of Group IIIa–Va of the Periodic Table such as

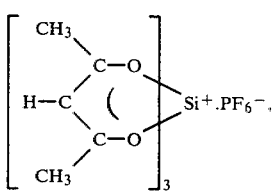

and the like. Furhter, as other cationic polymerization catalysts, there may be used Lewis acids such as $BF_3$, $FeCl_3$, $SnCl_4$, $SbCl_5$, $SbF_3$, $TiCl_4$ and the like; coordinated compounds of Lewis acid and a compound having O, S, N or the like such as $BF_3OEt_2$, $BF_3$-aniline complex and the like; oxonium salts, diazonium salts, and carbonium salts of Lewis acids; halogen compounds, mixed halogen compounds and perhalogenic acid derivatives; and so on.

The amount of the cationic polymerization catalyst used is preferably in the range of 0.001–10% by weight based on the weight of the composition.

The composition of this invention may additionally contain various additives. As said additives, there may be used glass fiber, carbon fiber, mica, quarz powder, calcium carbonate, cellulose, kaolinite, talc, aluminum powder, colloidal silica having a large specific surface area, powdery polyvinyl chloride, powdery polyolefins such as polyethylene and polypropylene, and the like. Further, it is also possible to further decrease the volume shrinkage by adding a filler such as silica, talc, calcium carbonate, alumina or the like.

Further, a non-reactive diluent, a flame-retardant, a flexibilizer and other modifying agents may optionally be incorporated into the curable composition of this invention. Examples of said flame-retardant include halogen-containing flame-retardants such as hexabromobenzene; inorganic flame-retardants such as hydrated alumina and phosphoric acid salts; and the like.

Examples of said non-reactive diluent include dibutyl phthalate, dioctyl phthalate, tricresyl phosphate, tar and the like.

Examples of said flexibilizer include polysulfides, polyamides, polyalkylene-polyols, elastomers and the like.

As mentioned above, the spiro-orthoester which is one of the essential constituents of the composition of this invention is characterized in that it can generally be easily synthesized by a simple reaction from a commercially available epoxy compound and γ-butyrolactone (n=3), δ-valerolactone (n=4) or ε-caprolactone (n=5) and, in addition, the volume shrinkage thereof on curing with an organic acid is very small.

For example, when a spiro-orthoester produced from γ-butyrolactone and an epoxy compound of the type of glycidyl ether of Bisphenol A (spiro-orthoester [A] of Referential Example 1 which appears hereinafter) is cured with methylhexahydrophthalic anhydride, the volume shrinkage is about 0.7%. When a spiro-orthoester produced from ε-caprolactone and an epoxy compound of the type of glycidyl ether of Bisphenol A (spiro-orthoester [B] of Referential Example 2 which appears hereinafter) is cured with dodecenylsuccinic anhydride, the volume shrinkage is about 0.7%. These values are much smaller than those of general thermosetting resins. Herein, the volume shrinkage (%) is expressed by [1 − (specific gravity of composition before polymerization/specific gravity of polymer)] × 100.

Since the composition of this invention has a very small volume shrinkage on curing, it is characterized in that it has a high dimensional accuracy when used as a molding material and it yields only a small strain of an embedded material due to the contraction of the composition, and gives a high adhesion to a mold, and no gap is formed when it is used as a casting material. When it is used as a coating material, only a very small internal strain is caused due to shrinkage, so that the adhesion of the coating to a substrate is excellent and the warpage is small. Further, when it is used as an adhesive, the internal strain due to shrinkage is very small, so that the internal stress is small and the bonding strength is high.

Moreover, the composition of this invention is characterized in that it exhibits a high peeling strength when used as an adhesive. For example, when aluminum plates are bonded to each other and coldrolled steel plates are bonded to each other by the use of a composition comprising a spiro-orthoester produced from ε-caprolactone and an epoxy compound of the type of glycidyl ether of Bisphenol A (spiro-orthoester [B] of Referential Example 2), and dodecenylsuccinic anhydride as a curing agent, the results of T-peeling test are so good that the respective T-peeling strengths are 12 kgf/25 mm and 7 kgf/25 mm.

Thus, the composition of this invention is quite useful as a casting material, a molding material, a composite material, an adhesive, a coating material and so on.

This invention will further be illustrated with reference to Referential Examples and Examples, wherein parts are by weight unless otherwise specified.

REFERENTIAL EXAMPLE 1

Production of Spiro-orthoester [A]

In a 500-ml, four-necked falsk equipped with a stirrer, a condenser, a thermometer and a dropping furnnel were placed 200 ml of methylene chloride and 103.2 g (1.2 moles) of γ-butyrolactone. The resulting solution was cooled to about 10° C. with ice water, to which 0.8 ml of BF$_3$OEt$_2$ was added. Then, a solution of 152 g (0.4 mole) of Epikote 828 (trade name of Shell Chemical Co., Ltd. for glycidyl ether of Bisphenol A having an epoxy equivalent of 184–194) in 100 ml of methylene chloride was added with stirring over a period of 1 hour. The resulting mixture was subjected to reaction at 25° C. for 4 hours, and then 1.6 ml of triethylamine was added to deactivate the catalyst.

In order to remove the excessive γ-butyrolactone, the reaction mixture was then washed with two portions of 500 ml of 5% aqueous soluton of sodium hydroxide and centrifuged to separate the organic layer. The organic layer was washed with 250 ml of distilled water, centrifuged and then dehydrated overnight on magnesium sulfate, after which the solvent was removed to obtain 188 g of spiro-orthoester [A].

This product was a colorless, transparent, viscous liquid having a specific gravity of 1.213 at 25° C. Its viscosity was about 250,000 centipoises at 50° C. The main component of the product is represented by the following structural formula:

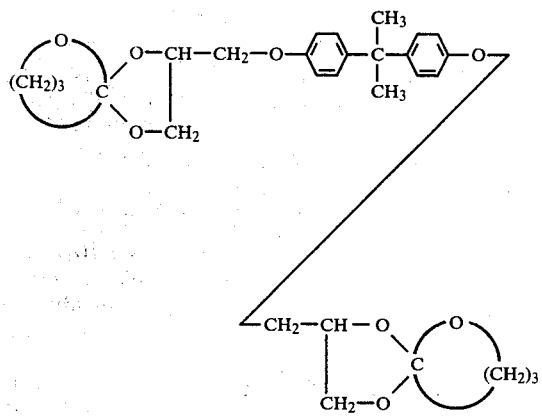

REFERENTIAL EXAMPLE 2

Production of Spiro-orthoester [B]

In a one-liter four-necked flask equipped with a stirrer, a condenser, a thermometer and a dropping funnel were placed 200 ml of methylene chloride and 136.8 g (1.2 moles) of ε-caprolactone. The resulting solution was cooled to about 10° C. with ice water, to which 1 ml of BF$_3$OEt$_2$ was added.

While keeping the mixture at a temperature of about 10° C., a solution of 114 g (0.3 mole) of Epikote 828 in 500 ml of methylene chloride was then dropped thereinto with stirring over a period of 5 hours. The mixture was subjected to reaction at this temperature for 3 hours, and 3 ml of triethylamine was then added to deactivate the catalyst.

In order to remove the excessive ε-caprolactone, the reaction mixture was then washed with two portions of 500 ml of 6% aqueous solution of NaOH, centrifuged, washed with two portions of 300 ml of distilled water and centrifuged. The organic layer was dehydrated overnight on magnesium sulfate, and the solvent was then removed to obtain 131 g of spiro-orthoester [B].

This product was a light yellow, transparent, viscous liquid having a specific gravity of 1.178 at 25° C. and a viscosity of about 98,000 centipoises at 50° C. The main component of the product is represented by the following structural formula:

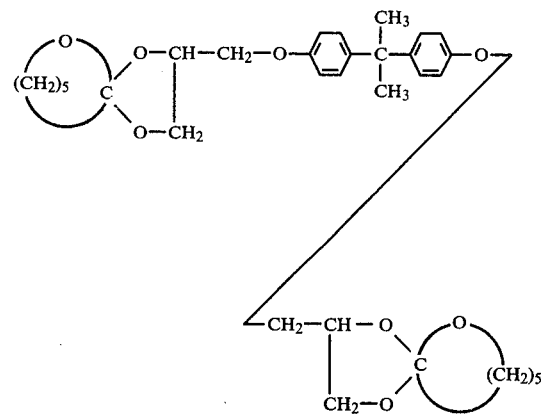

REFERENTIAL EXAMPLE 3

Production of Spiro-orthoester [C]

In a one-liter, four-necked flask equipped with a stirrer, a condenser, a thermometer and a dropping funnel were placed 200 ml of methylene chloride and 136.8 g (1.2 moles) of ε-caprolactone. The resulting solution was cooled to about 10° C. with ice water, to which 1 ml of BF$_3$OEt$_2$ was added.

While keeping the mixture at a temperature of about 10° C., a solution of 82 g (about 0.3 mole) of an alicyclic type epoxy resin represented by the chemical formula:

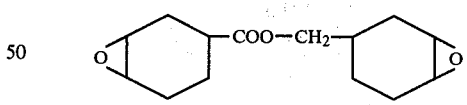

in 300 ml of methylene chloride was then dropped thereinto with stirring over a period of one hour. After the resulting mixture was subjected to reaction at this temperature for 3.5 hours, 3 ml of triethylamine was added thereto to deactivate the catalyst. In order to remove the excessive ε-caprolactone, the reaction mixture was then washed with two portions of 500 ml of 6% aqueous solution of NaOH, centrifuged, washed with two portions of 300 ml of distilled water and centrifuged. The organic layer was dehydrated overnight on magnesium sulfate and the solvent was then removed to obtain 101 g of spiro-orthoester [C].

This product was a light yellow, transparent, semi-solid material having a specific gravity of 1.211 at 25° C. and a viscosity of 1,700,000 centipoises at 60° C.

The main component of the product is represented by the following structural formula:

$$\text{(CH}_2)_5\text{C}\begin{pmatrix}O\\O\end{pmatrix}\begin{pmatrix}O\\O\end{pmatrix}\text{—COO—CH}_2\text{—}\begin{pmatrix}O\\O\end{pmatrix}\begin{pmatrix}O\\O\end{pmatrix}\text{C(CH}_2)_5$$

EXAMPLE 1

To 100 parts of spiro-orthoester [A] were added 27 parts of methylhexahydrophthalic anhydride as a curing agent and 1.3 parts of N-cyanomethyl-2-methylimidazole as a curing accelerator, and the resulting mixture was cured at 120° C. for 2 hours and then at 150° C. for 4 hours to obtain a cured product.

The Shore hardness of this cured product was D-72. As determined from the specific gravity at 25° C. of the composition before the curing and that of the cured product, the volume shrinkage on curing was as small as about 0.7%.

EXAMPLE 2

To 100 parts of spiro-orthoester [B] were added 39 parts of dodecenylsuccinic anhydride as a curing agent and 1.4 parts of N-cyanomethyl-2-methylimidazole as a curing accelerator, and the resulting mixture was cured in the same manner as in Example 1 to obtain a cured product.

The Shore hardness of this cured product was D-72. The volume shrinkage on curing was as small as about 0.7%.

EXAMPLE 3

To 100 parts of spiro-orthoester [C] were added 38 parts of hexahydrophthalic anhydride as a curing agent and 1.4 parts of tris(dimethylaminomethyl)-phenol as a curing accelerator, and the resulting mixture was cured in the same manner as in Example 1 to obtain a cured product.

The Shore hardness of this cured product was D-70. The volume shrinkage on curing was nearly zero.

EXAMPLE 4

Using compositions having the formulations shown in Table 1, aluminum plates (0.6 mm in thickness) were bonded to each other and cold-rolled steel plates (JIS G-3141 SPCCD) (0.3 mm in thickness) were bonded to each other, and their T-peeling strengths were measured.

The bonding was carried out under the curing conditions mentioned in Example 1, and the T-peeling strength was measured according to the method of JIS K 6854-1977. The adherends were previously defatted with acetone prior to the bonding.

TABLE 1

| Item | | Composition of this invention | Control composition |
|---|---|---|---|
| Formulation | Spiro-orthoester [B] | 100 parts | — |
| | Epikote 828 | — | 100 parts |
| | Dodecenylsuccinic anhydride | 39 parts | 126 parts |
| | N—cyanomethyl-2-methylimidazole | 1.4 parts | 2.2 parts |
| Bonding test | T-Peeling strengths [kgf/25 mm] Aluminum plate | 12 | 1.3 |
| | Cold rolled steel plate | 7 | 0.7 |

It is apparent from the above-mentioned results that the composition of this invention is markedly superior to the control composition free from spiro-orthoester in bonding strength.

EXAMPLE 5

Using compositions having the formulations shown in Table 2, the bonding of iron to iron and glass to glass (5 mm in thickness) was carried out and the tensile shear strengths were measured.

The bonding was carried out by curing the composition at 120° C. for 5 hours and then at 150° C. for 2 hours, and the tensile shear strengths were measured according to the method of JIS K 6850-1977. The iron used as the test piece was previously surface-treated by means of sandblasting with alumina #100, and the glass was previously defatted with acetone.

TABLE 2

| Item | | Composition of this invention | |
|---|---|---|---|
| Formulation | Spiro-orthoester [A] | 100 parts | — |
| | Spiro-orthoester [B] | — | 100 parts |
| | Methylhexahydrophthalic anhydride | 27 parts | — |
| | Dodecenylsuccinic anhydride | — | 39 parts |
| | N—cyanomethyl-2-methylimidazole | 1.3 parts | 1.4 parts |
| Bonding test | Tensile shear strength [kgf/cm²] Fe - Fe | 180 | 190 |
| | Glass - Glass | *76 | *70 |

*Failure of body

EXAMPLE 6

To a mixture of 90 parts of spiro-orthoester [A] and 10 parts of 2-chloromethyl-1,4,6-trioxaspiro-[4,6]undecane were added 60 parts of methyl-3,6-endomethylene-1,2,3,6-tetrahydrophthalic anhydride as a curing agent and 1.6 parts of tris(dimethylaminomethyl)phenol as a curing accelerator, and the mixture was cured in the same manner as in Example 1 to obtain a cured product.

The Shore hardness of this cured product was D-50. The volume shrinkage on curing was about 0.9%.

EXAMPLE 7

To a mixture of 80 parts of spiro-orthoester [B] and 20 parts of 2-methylene-1,4,6-trioxaspiro[4,6]-undecane were added 91 parts of dodecenylsuccinic anhydride as a curing agent and 1.9 parts of N-cyanomethyl-2-methylimidazole as a curing accelerator, and the resulting mixture was cured in the same manner as in Example 1 to obtain a hard cured product. The Shore hardness of this cured product was D-65. The volume shrinkage on curing was about 0.8%.

EXAMPLE 8

Compositions having the formulations shown in Table 3 were prepared by adding dodecenylsuccinic anhydride as a curing agent and N-cyanomethyl-2-methylimidazole as a curing accelerator to spiro-orthoester [B]. The compositions were cured at 120° C. for 3 hours and then at 150° C. for 4 hours. The cured products thus obtained were tested for Shore hardness and subjected to acetone immersion test. The results obtained are shown in Table 3.

TABLE 3

| Item | Composition | | | | Properties of cured product | | | |
|---|---|---|---|---|---|---|---|---|
| | Spiro-orthoester [B] (part) | Dodecenyl-succinic anhydride (part) | *1 Curing accelerator (part) | *2 Equivalent ratio of charged materials | State | Shore hardness | *3 Acetone immersion test | |
| | | | | | | | Degree of dissolution (%) | *4 Degree of swelling (%) |
| Run No. 1 | 100 | 131 | 2.3 | 1.5 | Solid | D-60 | 9.4 | 82 |
| Run No. 2 | 100 | 110 | 2.1 | 1.25 | " | D-72 | 5.7 | 60 |
| Run No. 3 | 100 | 88 | 1.9 | 1.0 | " | D-80 | 3.6 | 52 |
| Run No. 4 | 100 | 66 | 1.7 | 0.75 | " | D-73 | 2.2 | 54 |
| Run No. 5 | 100 | 44 | 1.4 | 0.5 | " | D-72 | 8.6 | 75 |
| Run No. 6 | 100 | 22 | 1.2 | 0.25 | " | D-68 | 39 | 150 |
| Run No. 7 | 100 | 11 | 1.1 | 0.12 | Viscous | — | 100 | — |
| Run No. 8 | 100 | 4.4 | 1.0 | 0.05 | " | — | 100 | — |

Note:
*1 N—cyanomethyl-2-methylimidazole

*2 $\dfrac{\text{(Moles of dodecenylsuccinic anhydride in composition)}}{\text{(Equivalents of spiro-orthoester group in composition)}}$

*3 Acetone immersion test: Sample was immersed in acetone at room temperature for 24 hours, and the soluble fraction and the degree of swelling were measured.

*4 $\left\{ \dfrac{\text{(Weight after swelling)}}{\text{(Weight of original sample)} - \text{(Weight of dissolved fraction)}} - 1 \right\} \times 100$

EXAMPLE 9

To a mixture of 50 parts of Epikote 828 and 50 parts of spiro-orthoester [A] was added 3 parts of monoethylamine complex of $BF_3$ as a cationic polymerization catalyst. The resulting mixture was cured at 120° C. for 4 hours and then at 150° C. for 6 hours.

The Shore hardness of this cured product was D-86. As determined from the specific gravity at 25° C. of the composition and that of the cured resin, the volume shrinkage on curing was as small as about 2.4%.

COMPARATIVE EXAMPLE 1

To 100 parts of Epikote 828 was added 3 parts of monoethylamine complex of $BF_3$, and polymerization was carried out under the same conditions as in Example 9.

The Shore hardness of the cured product was D-89. The volume shrinkage on curing reached about 3.7%.

EXAMPLE 10

To a mixture of 50 parts of Epikote 828 and 50 parts of spiro-orthoester [B] were added 54 parts of dodecenylsuccinic anhydride as an organic acid curing agent and 1.5 parts of N-cyanomethyl-2-methylimidazole as a curing accelerator. The resulting mixture was cured at 120° C. for 4 hours and then at 150° C. for 6 hours.

The Shore hardness of the cured product was D-82. The volume shrinkage on curing was about 2.3%.

EXAMPLE 11 AND COMPARATIVE EXAMPLE 2

Using compositions having the formulations shown in Table 4, the bonding of aluminum plates to each other (0.6 mm in thickness) and cold-rolled steel plates to each other (JIS G-3141 SPCCD, 0.3 mm in thickness) was carried out under the same curing conditions as in Example 10, and T-peeling strengths were measured according to JIS K 6854-1977. The adherends used were previously defatted with acetone. The results obtained are shown in Table 4.

TABLE 4

| | Item | | Example 11 | Comparative Example 2 |
|---|---|---|---|---|
| Formulation | Epikote 828 | | 50 parts | 100 parts |
| | Spiro-orthoester [B] | | 50 parts | — |
| | Dodecenylsuccinic anhydride | | 83 parts | 126 parts |
| | N—cyanomethyl-2-methylimidazole | | 1.8 parts | 2.2 parts |
| Bonding test | T-Peeling strength (kgf/25 mm) | Aluminum plate | 2.5 | 1.3 |
| | | Cold-rolled steel plate | 1.9 | 0.7 |

The composition of this invention comprising spiro-orthoester [B] exhibited a bonding strength of at least about twice that of the composition outside the scope of this invention.

EXAMPLES 12 AND 13

Using compositions having the formulations shown in Table 5, the bonding of iron to iron and glass to glass (5 mm in thickness) was carried out, and the tensile shear strengths were measured.

The bonding was carried out by applying the composition and then curing it at 120° C. for 5 hours and then at 150° C. for 2 hours, and the tensile shear strength was measured according to JIS K 6850-1977. The results obtained are shown in Table 5.

The iron used as the test piece was previously surface-treated by sandblasting with alumina #100, and the glass was previously defatted with acetone.

TABLE 5

| | Item | | Example 12 | Example 13 |
|---|---|---|---|---|
| Formulation | Epikote 828 | | 50 parts | 50 parts |
| | Spiro-orthoester [A] | | 50 parts | — |
| | Spiro-orthoester [B] | | — | 50 parts |
| | Monoethylamine complex of $BF_3$ | | 3 parts | — |
| | Methylhexahydrophthalic anhydride | | — | 54 parts |
| | N—cyanomethyl-2-methylimidazole | | — | 1.5 parts |
| Bonding test | Tensile shear strength (kgf/cm²) | Fe - Fe | 190 | 200 |
| | | Glass - Glass | *70 | *75 |

*Failure of body

EXAMPLE 14

A composition comprising 50 parts of 2-phenoxymethyl-1,4,6-trioxaspiro[4,4]nonane, 50 parts of Adeka Resin EP-4080 (trade name of Asahi Denka Kogyo K.K. for hydrogenated Bisphenol A type epoxy resin having an epoxy equivalent of 235–255) and 3 parts of monoethylamine complex of $BF_3$ was cured at 120° C. for 5 hours to obtain a soft cured product.

The volume shrinkage on curing was about 2.6%.

EXAMPLE 15

To a mixture comprising 50 parts of 2-methylene-1,4,6-trioxaspiro[4,6]undecane and 50 parts of polyglycidyl ether of glycerin were added 97 parts of hexahydrophthalic anhydride as an organic acid curing agent and 2.0 parts of tris(dimethylaminomethyl)phenol as a curing accelerator. The composition thus obtained was cured by keeping it at 120° C. for 5 hours and then at 150° C. for 3 hours. The Shore hardness of this cured product was A-65. The volume shrinkage on curing was 4.6%.

COMPARATIVE EXAMPLE 3

To 100 parts of polyglycidyl ether of glycerin were added 103 parts of hexahydrophthalic anhydride as a curing agent and 2.0 parts of tris(dimethylaminomethyl)phenol as a curing accelerator. The composition thus obtained was cured in the same manner as in Example 15 to obtain a hard cured product.

The volume shrinkage on curing was about 6%.

EXAMPLE 16

To a mixture comprising 50 parts of alicyclic epoxy resin "Chissonox 289" and 50 parts of spiro-orthoester [C] were added 51 parts of hexahydrophthalic anhydride as a curing agent and 1.5 parts of tris(dimethylaminomethyl)phenol as a curing accelerator. The composition thus obtained was cured by keeping it at 120° C. for 4 hours and then at 150° C. for 6 hours.

The Shore hardness of this cured product was D-85. The volume shrinkage on curing was about 2.6%.

What is claimed is:

1. A curable composition comprising:
   (A) at least one spiro-orthoester compound having at least one spiro-orthoester group represented by the formula:

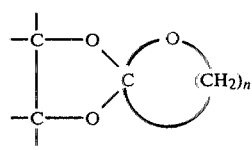

[I]

wherein n is an integer of 3–5,
   (B) at least one curing agent selected from the group consisting of organic polybasic acids and their anhydrides.

2. A curable composition comprising:
   (A) at least one spiro-orthoester compound having at least one spiro-orthoester group represented by the formula:

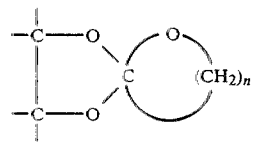

[I]

wherein n is an integer of 3–5,
   (B) at least one curing agent selected from the group consisting of organic polybasic acids and their anhydrides, and
   (C) an epoxy compound having at least one epoxy group.

3. A curable composition according to claim 2, which further comprises (D) a cationic polymerization catalyst.

4. A curable composition according to claim 1, wherein the amount of ingredient (B) is 0.1–1.5 equivalents per equivalent of the spiro-orthoester group.

5. A curable composition according to claim 2 or 3, wherein the amount of ingredient (B) is 0.1–1.5 equivalents per equivalent of the total sum of the equivalent of spiro-orthoester group and the equivalent of epoxy group.

6. A curable composition according to claim 1, wherein the amount of ingredient (B) is 0.3–1.2 equivalents per equivalent of the spiro-orthoester group.

7. A curable composition according to claim 2 or 3, wherein the amount of ingredient (B) is 0.3–1.2 equivalents per equivalent of the total sum of the equivalent of spiro-orthoester group and the equivalent of epoxy group.

8. A curable composition according to claim 2 or 3, wherein the amount of ingredient (C) is 90–5% by weight based on the weight of the spiro-orthoester.

9. A curable composition according to claim 5, wherein the amount of ingredient (C) is 90–5% by weight based on the weight of the spiro-orthoester.

10. A curable composition according to claim 2 or 3, wherein the amount of ingredient (C) is 70–10% by weight based on the weight of the spiro-orthoester.

11. A curable composition according to claim 7, wherein the amount of ingredient (C) is 70–10% by weight based on the weight of the spiro-orthoester.

12. A curable composition according to claim 3, wherein the amount of ingredient (D) is 0.001–10% by weight based on the weight of the composition.

13. A curable composition according to claim 12, wherein the amount of ingredient (B) is 0.1–1.5% equivalents per equivalent of the total sum of the equivalent of spiro-orthoester group and the equivalent of epoxy group.

14. A curable composition according to claim 12, wherein the amount of ingredient (B) is 0.3–1.2 equivalent per equivalent of the total sum of the equivalent of spiro-orthoester group and the equivalent of epoxy group.

15. A curable composition according to claim 13, wherein the amount of ingredient (C) is 90–5% by weigh based on the weight of the spiro-orthoester.

16. A curable composition according to claim 14, wherein the amount of ingredient (C) is 70–10% by weight based on the weight of spiro-orthoester.

17. A curable composition according to claim 1, 2 or 3, wherein spiro-orthoester compound (A) is represented by the following formula:

$$Y-X)_m \qquad [II]$$

wherein m is an integer of at least 1; X is

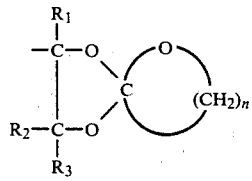

or

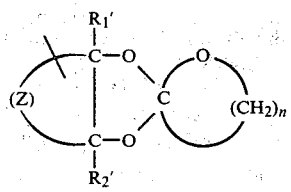

wherein (Z) is a substituted or unsubstituted cycloalkylene group, n is an integer of 3-5, and $R_1$, $R_2$, $R_3$, $R_1'$ and $R_2'$ are independently hydrogen atoms, alkyl groups, haloalkyl groups or alkenyl groups; and Y represents the residue formed by depriving an epoxy compound of the epoxy group; and Y and $R_1$ may, when taken together, form a methylene group.

18. A curable composition according to claim 1, 2 or 3, wherein said spiro-orthoester is 1,4,6-trioxaspiro[4,4-]nonane, 2-methyl-1,4,6-trioxaspiro [4,4]nonane, 2-chloromethyl-1,4,6-trioxaspiro[4,4]nonane, 2-phenoxymethyl-1,4,6-trioxaspiro[4,4]nonane, 1,4,6,-trioxaspiro-[4,5]decane, 2-chloromethyl-1,4,6,-trioxaspiro[4,6]-undecane, 2,3-dimethyl-1,4,6-trioxaspiro[4,6]undecane, 2-methylene-1,4,6-trioxaspiro[4,4]nonane, 2-methylene-1,4,6-trioxaspiro[4,6]undecane or 2-phenyl-1,4,6-trioxaspiro[4,6]undecane.

19. A curable composition according to claim 1, 2 or 3, wherein said spiro-orthoester is a spiro-orthoester produced by reacting a lactone with an epoxy resin having, on the average, at least one glycidyl ether group or β-methylglycidyl ether group in the molecule obtained by reacting epichlorohydrin or β-methylepichlorohydrin with 2,2-bis(4'-hydroxyphenyl)propane, halogenated 2,2-bis(4'-hydroxyphenyl)propane, bis(4-hydroxyphenyl)-methane, resorcinol, tetrahydroxyphenylmethane; a novolac type polyfunctional phenol obtained by the condensation of phenol or cresol with formaldehyde; phenol, cresol, t-butylphenol, butyl alcohol, allyl alcohol, ethylene glycol, polyethylene glycol, 2,2-bis(4'-hydroxycyclohexyl)propane, glycerin or 1,1,1-trimethylolpropane; or a spiro-orthoester produced by reacting a lactone with an epoxy resin having, on the average, at least one glycidyl ester group or β-methylglycidyl ester group in the molecule obtained by reacting epichlorohydrin or β-methylepichlorohydrin with benzenemonocarboxylic acid, adipic acid, sebacic acid, phthalic acid, hexahydrophthalic acid or tetrahydrophthalic acid; or a spiro-orthoester produced from a lactone and an alicyclic epoxy compound having, on the average, at least one endo-epoxy group in the molecule; or a spiro-orthoester produced from a lactone and an epoxidized olefin, epoxidized polybutadiene, an epoxidized vegetable oil, a nitrogen-containing epoxy compound, or a nitrogen-containing heterocyclic epoxy compound obtained from an isocyanuric acid derivative, a hydantoin derivative or an imidazoline derivative; or a mixture thereof.

20. A curable composition according to claim 1, 2 or 3 wherein said spiro-orthoester compound (A) is a compound represented by one of the following formulas:

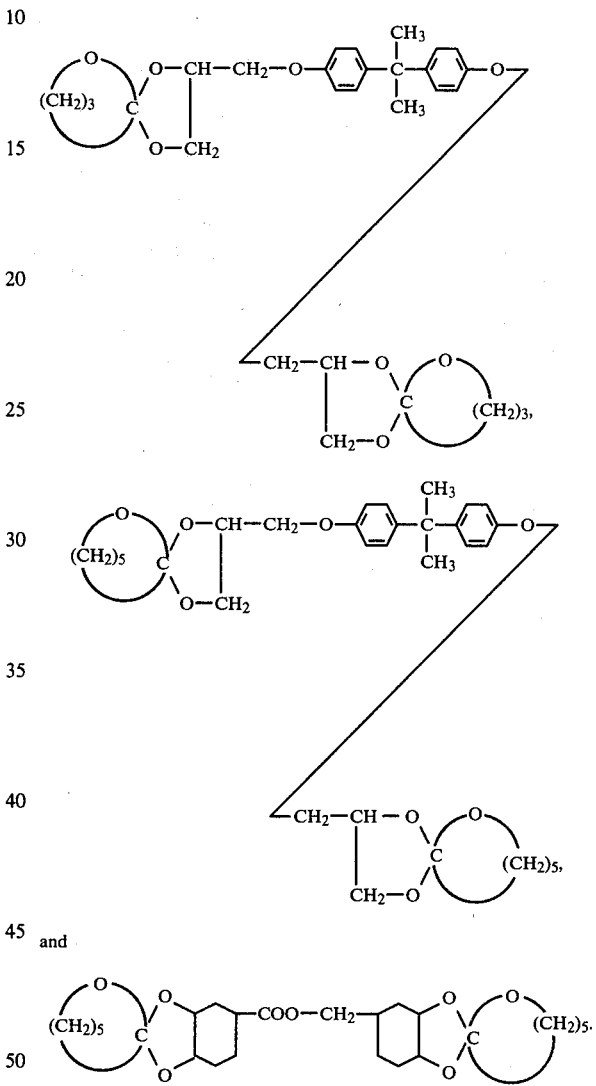

and

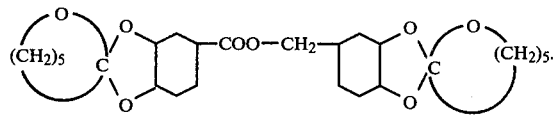

21. A curable composition according to claim 1, 2 or 3, wherein said curing agent (B) is succinic acid, methylsuccinic acid, dodecenylsuccinic acid, dichlorosuccinic acid, azelaic acid, sebacic acid, itaconic acid, maleic acid, citraconic acid, phthalic acid, tetrahydrophthalic acid, methyltetrahydrophthalic acid, hexahydrophthalic acid, methylhexahydrophthalic acid, endomethylenetetrahydrophthalic acid, methylendomethylenetetrahydrophthalic acid, tricarballylic acid, trimellitic acid, pyrometllitic acid, cyclopentane-1,2,3,4-tetracarboxylic acid, benzophenone-3,3',4,4'-tetracarboxylic acid, an anhydride thereof, a mixture of two or more of the above-mentioned acids, or a mixture of the above-mentioned acid and a monobasic acid anhydride.

22. A curable composition according to claim 1, 2 or 3, wherein said curing agent (B) is methylhexahydrophthalic anhydride, decenylsuccinic anhydride, hexahydrophthalic anhydride, dodecenylsuccinic anhydride, or methyl-3,6-endomethylene-1,2,3,6-tetrahydrophthalic anhydride.

23. A curable composition according to claim 2 or 3, wherein said epoxy compound (C) is glycidyl ether, β-methylglycidyl ether, polyglycidyl ether or poly(β-methylglycidyl) ether obtained by reacting epichlorohydrin or β-methylepichlorohydrin with 2,2-bis-(4'-hydroxyphenyl)propane, halogenated 2,2-bis(4'-hydroxyphenyl)propane, bis(4-hydroxyphenyl)methane, resorcinol, tetrahydroxyphenylmethane, a novolac type polyfunctional phenol obtained by the condensation of phenol or cresol with formaldehyde, phenol, cresol, t-butylphenol, butyl alcohol, allyl alcohol, ethylene glycol, polyethylene glycol, 2,2-bis(4'-hydroxycyclohexyl)propane, glycerin or 1,1,1-trimethylolpropane; or glycidyl ester or β-methylglycidyl ester, polyglycidyl ester or poly(β-methylglycidyl) ester obtained by reacting epichlorohydrin or β-methylepichlorohydrin with benzenemonocarboxylic acid, adipic acid, sebacic acid, phthalic acid, hexahydrophthalic acid, or tetrahydrophthalic acid; or an epoxidized olefin, epoxidized polybutadiene, an epoxidized vegetable oil, an epoxidized cyclopentadiene compound, an aniline-modified epoxy compound, or a nitrogen-containing heterocyclic epoxy compound obtained from an isocyanuric acid derivative, a hydantoin derivative or an imidazoline derivative; or styrene oxide obtained from a monounsaturated compound; or an endo-epoxy type compound synthesized by the oxidation of intramolecular double bond.

24. A curable composition according to claim 2 or 3, wherein said epoxy compound (C) is glycidyl ether of Bisphenol A, hydrogenated Bisphenol A type epoxy resin, polyglycidyl ether of glycerin, or alicyclic epoxy resin.

25. A curable composition according to claim 3, wherein said cationic polymerization catalyst (D) is

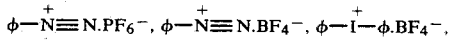

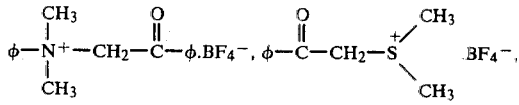

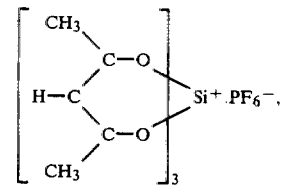

BF$_3$, FeCl$_3$, SnCl$_4$, SbCl$_5$, SbF$_3$, TiCl$_4$, BF$_3$OEt$_2$, BF$_3$-aniline complex; an oxonium salt, a diazonium salt or a carbonium salt of a Lewis acid; a halogen compound, a mixed halogen compound or a perhalogenic acid derivative.

26. A curable composition according to claim 1, 2 or 3, which additionally contains a curing accelerator.

27. A curable composition according to claim 26, wherein said curing accelerator is a tertiary amine, a quaternary ammonium salt, an imidazole compound, pyridine, dicyandiamide, a chelate compound or metallocene.

28. A curable composition according to claim 26, wherein said curing accelerator is contained in a proportion of 0.2–3 parts by weight per 100 parts by weight of the total weight of the spiro-orthoester compound (A), the curing agent (B) and the epoxy compound (C).

29. A curable composition according to claim 27, wherein said curing accelerator is contained in a proportion of 0.2–3 parts by weight per 100 parts by weight of the total weight of the spiro-orthoester compound (A), the curing agent (B) and the epoxy compound (C).

* * * * *